(12) United States Patent
Thibault et al.

(10) Patent No.: US 9,460,485 B2
(45) Date of Patent: Oct. 4, 2016

(54) SYSTEMS AND METHODS FOR GUIDED DE-NOISING FOR COMPUTED TOMOGRAPHY

(71) Applicant: General Electric Company, Schenectady, NY (US)

(72) Inventors: Jean-Baptiste Thibault, Waukesha, WI (US); Debashish Pal, Waukesha, WI (US); Jie Tang, Waukesha, WI (US); Ken David Sauer, South Bend, IN (US); Charles Bouman, Lafayette, IN (US); Ruoqiao Zhang, Lafayette, IN (US)

(73) Assignees: GENERAL ELECTRIC COMPANY, Schenectady, NY (US); UNIVERSITY OF NOTRE DAME DU LAC, Notre Dame, IN (US); PURDUE RESEARCH FOUNDATION, Lafayette, IN (US)

( * ) Notice: Subject to any disclaimer, the term of this patent is extended or adjusted under 35 U.S.C. 154(b) by 116 days.

(21) Appl. No.: 14/566,874

(22) Filed: Dec. 11, 2014

(65) Prior Publication Data

US 2016/0171648 A1 Jun. 16, 2016

(51) Int. Cl.
*G06T 3/00* (2006.01)
*G01N 23/04* (2006.01)
*G01T 1/36* (2006.01)
*G01N 23/087* (2006.01)
*G06T 5/10* (2006.01)

(52) U.S. Cl.
CPC ............ *G06T 3/0056* (2013.01); *G01N 23/046* (2013.01); *G01N 23/087* (2013.01); *G01T 1/36* (2013.01); *G06T 5/10* (2013.01); *G06T 2207/10004* (2013.01); *G06T 2207/10081* (2013.01)

(58) Field of Classification Search
CPC ....... G06T 3/0056; G06T 5/002; G06T 5/50; G06T 11/008; G06T 2207/10081; G06T 2211/408; G01N 23/046; G01N 23/083; G01N 23/087
See application file for complete search history.

(56) References Cited

U.S. PATENT DOCUMENTS 8,787,519 B2   7/2014  Fan et al. ............... A61B 6/482
9,330,443 B1 * 5/2016  Zou et al. ............... G06T 5/002
                                                           382/131

(Continued)

OTHER PUBLICATIONS

Wu et al., Monochromatic CT Image Representation via Fast Switching Dual kVp, Feb. 9, 2009, SPIE, vol. 7258, pp. 45-1 to 45-8.
Zou et al., Analysis of Fast kV-switching in Dual Energy CT using a Pre-reconstruction Decomposition Technique, 2008, SPIE, vol. 6913, pp. 13-1 to 13-12.

(Continued)

*Primary Examiner* — Andrew W Johns
(74) *Attorney, Agent, or Firm* — Dean D. Small; The Small Patent Law Group, LLC

(57) ABSTRACT

A method includes obtaining spectral computed tomography (CT) information via an acquisition unit having an X-ray source and a CT detector. The method also includes, generating, with one or more processing units, using at least one image transform, a first basis image and a second basis image using the spectral CT information. Further, the method includes performing, with the one or more processing units, guided processing on the second basis image using the first basis image as a guide to provide a modified second basis image. Also, the method includes performing at least one inverse image transform using the first basis image and the modified second basis image to generate at least one modified image.

20 Claims, 7 Drawing Sheets

(56) References Cited

U.S. PATENT DOCUMENTS

| | | | |
|---|---|---|---|
| 2009/0052612 A1* | 2/2009 | Wu et al. | 378/5 |
| 2009/0135998 A1* | 5/2009 | Rossl et al. | 378/98 |
| 2012/0134561 A1 | 5/2012 | Xu et al. | 382/131 |

OTHER PUBLICATIONS

Kalender et al., "An Algorithm for Noise Suppression in Dual Energy CT Material Density Images," IEEE Transactions on Medical Imaging, vol. 7, No. 3, Sep. 1988, pp. 218-224.

International Search Report and Written Opinion from corresponding PCT application PCT/US2015/054659 dated Mar. 9, 2016; 13 pages.

Michael Manhart et al., "Guided Noise Reduction for Spectral CT with Energy-Selective Photon Counting Detectors", Proceedings of the Third International Conference on Image Formation in X-ray Computed Tomography, Jun. 22, 2014, pp. 91-94.

Kalender W A et al., "An Algorithm for Noise Suppression in Dual Energy CT Material Density Images", IEEE Transactions on Medical Imaging, IEEE Service Center, Piscataway, NJ, US, vol. 7, No. 3, Sep. 1988; pp. 218-224.

* cited by examiner

SYSTEMS AND METHODS FOR GUIDED DE-NOISING FOR COMPUTED TOMOGRAPHY

BACKGROUND OF THE INVENTION

The subject matter disclosed herein relates generally to systems and methods for computed tomography (CT) imaging.

In CT imaging, an X-ray source may be rotated around an object to obtain imaging information. X-rays from the source attenuated by the object may be collected or detected by a detector and used to reconstruct an image. Due to variations in attenuation as a function of energy level among materials, spectral CT imaging provides the ability to distinguish different materials even if the materials have similar attenuation for conventional single-energy CT scans at a given energy. Spectral CT imaging may be used to provide synthetic monochromatic images using linear combinations of material decomposed (MD) images. However, the raw MD images (i.e., water and iodine), as the direct results of filtered back-projection, may suffer significant amounts of negatively correlated noise resulting from projection-space material decomposition. Subsequent steps for noise reduction may thus be required. At some energies, one or the other of the MD images may tend to dominate, while at other energies the negatively correlated noise may essentially be cancelled. When one of the MD images tends to dominate, additional noise reduction may be required to keep noise at acceptable levels in synthesized monochromatic images while preserving spatial resolution and image quality (IQ).

Conventional noise reduction approaches may not achieve consistently lower noise in synthetic monochromatic images across all photon energy levels, as compared to raw MD images. For example, if conventionally de-noised MD images are combined, the noise of the resulting monochromatic image may contain more noise than the combination of raw MD images for a range of photon energies. Raw and de-noised images may be blended when producing monochromatic images, in order to select which MD images (raw or de-noised) should be combined to produce lower noise across an entire energy range. However, such blending results in unnecessarily large memory usage and storage requirements, as the information to de-noise images on-the-fly is stored along with the raw MD image information. Further, conventional de-noising approaches may not achieve sufficient noise reduction at low dosage levels, and/or may introduce artifacts that compromise image texture and spatial resolution.

BRIEF DESCRIPTION OF THE INVENTION

In one embodiment, a method is provided that includes obtaining spectral computed tomography (CT) information via an acquisition unit having an X-ray source and a CT detector. The method also includes, generating, with one or more processing units, using at least one image transform, a first basis image and a second basis image using the spectral CT information. Further, the method includes performing, with the one or more processing units, guided processing (e.g., de-noising) on the second basis image using the first basis image as a guide to provide a modified second basis image. Also, the method includes performing at least one inverse image transform using the first basis image and the modified second basis image to generate at least one modified image.

In another embodiment, an imaging system is provided that includes a computed tomography (CT) acquisition unit and a processing unit. The CT acquisition unit includes an X-ray source and a CT detector configured to collect spectral CT information of an object to be imaged. The X-ray source and the CT detector are configured to be rotated about the object to be imaged and to collect a series of projections of the object at plural energy levels as the X-ray source and CT detector rotate about the object to be imaged. The processing unit includes at least one processor operably coupled to the CT acquisition unit. The processing unit is configured to control the CT acquisition unit to collect the spectral CT information of the object to be imaged. The processing unit is also configured to generate, using at least one image transform, a first basis image and a second basis image using the spectral CT information. Further, the processing unit is configured to perform guided processing on the second basis image using the first basis image as a guide to provide a modified second basis image. Further, the processing unit is also configured to perform at least one inverse transform using the first basis image and the modified second basis image to generate at least one modified image.

In another embodiment, a tangible and non-transitory computer readable medium is provided that includes one or more computer software modules configured to direct one or more processors to obtain spectral computed tomography (CT) information via an acquisition unit comprising an X-ray source and a CT detector; generate, using at least one image transform, a first basis image and a second basis image using the spectral CT information; perform guided processing on the second basis image using the first basis image as a guide to provide a modified second basis image; and perform at least one inverse image transform using the first basis image and the modified second basis image to generate at least one modified image.

DETAILED DESCRIPTION OF THE INVENTION

Figure 1:
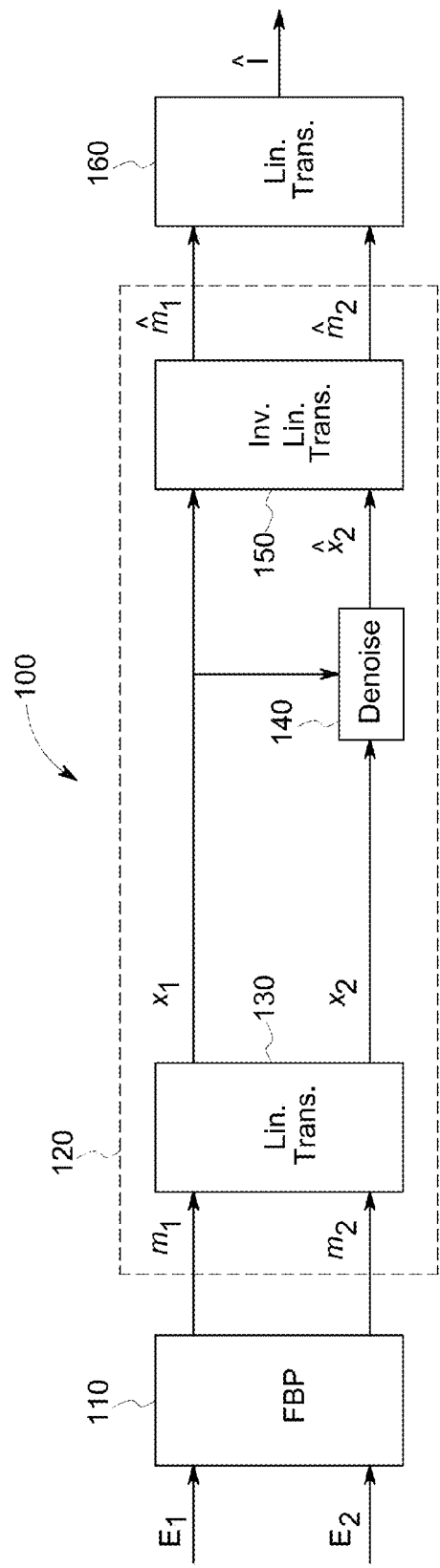
FIG. 1 illustrates a schematic process flow for guided de-noising in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for reduction of noise in material decomposition images and/or images (e.g., synthetic monochromatic images) formed or generated using material decomposition images. Various embodiments utilize noise reduction algorithms or techniques that reduce correlated noise in spectral (e.g., dual energy) CT images. Some embodiments utilize performance of de-noising in a transformed domain where correlated noise is approximately de-correlated. For example, in some embodiments, a linear transformation is first conducted to convert raw MD images to an alternative domain (e.g., two MD images may be combined to provide two transformed images), where the transform is configured to provide low correlated noise (e.g., approximately minimal) in one of the transformed images but a relatively large amount of noise in the other transformed image. Then, the image with the lower amount of correlated noise (e.g., a first transformed image or a first basis image) may be used as a guide to de-noise the image with larger amount of correlated noise (e.g., a second transformed image or second basis image). Next, the first transformed image (the image with the lower amount of correlated noise) and the de-noised second transformed image may be transformed back to MD domain to obtain de-noised MD images. Further, one or more synthetic monochromatic images may be generated using a linear combination of the de-noised MD images. In some embodiments, the transform used to provide the transformed images (or basis images for the de-noising of a second basis image guided by a first basis image) from the raw material images may be the same or similar to the transform used to provide a monochromatic image from the de-noised material images, while in other embodiments the transforms may be different.

In various embodiments, noise may be reduced utilizing a principle of negative noise correlation that may exist in MD images after a material decomposition process, for example, by applying a linear transform to provide basis images. For example, from raw material decomposition images, a 70 keV equivalent monochromatic image may be created by adding the material decomposition images to provide a first transformed or first basis image, while a second transformed image or second basis image may be formed from a subtraction of the MD images. In the addition image, the correlated noise cancels out, leading to a low-noise high signal image in the monochromatic domain. In the subtraction image, the correlated noise is doubled and the image corresponds to a differential signal. The subtraction image may then be relatively easier to de-noise than either of the raw MD images. For example, the addition image may be used as a guide to determine features such as organ edges that should be preserved in the subtraction image, or features across which filtering should not take place. After the subtraction image is de-noised, an inverse linear transformation using the addition image and the de-noised subtraction image may be applied to convert the images back to the MD domain, which results in de-noised MD images. In various embodiments, one or more additional de-noising steps (or other processing steps such as edge enhancement) may be performed for further image quality enhancement.

It may be noted that other images and/or transforms may be employed with guided de-noising in various embodiments. For example, transforms other than addition or subtraction may be used to provide the transformed or basis images. As another example, in dual-energy CT, generally a first projection obtained at a higher energy will have a lower noise level than a second projection obtained at a lower energy. Accordingly, in various embodiments, high-energy projection data may be used to de-noise low-energy projection data. Generally, in various embodiments, guided de-noising of a second image using a first image may include applying a filter to the second image, with the filter least in part being defined as a function of the first image. For example, a weighting applied to a given pixel of the second image may be a function of a corresponding pixel or group of pixels of the first image.

Various embodiments provide improved imaging, e.g. via improved de-noising or noise reduction. A technical effect of at least one embodiment includes reduced noise in material decomposition images and/or reduced noise in synthetic monochromatic images formed from material decomposition images. A technical effect of at least one embodiment includes providing reduced noise with relatively low computational requirements. A technical effect of at least one embodiment includes elimination or reduction of cross-contamination of noise between MD images and monochromatic images relative to conventional techniques. A technical effect of at least one embodiment includes providing improved noise reduction across all energies of a range. A technical effect of at least one embodiment includes allowing the use of lower radiation dosages for scans without compromising image quality or diagnostic capability (e.g., due to improved noise reduction). A technical effect of at least one embodiment includes avoidance or reduction of image artifacts, resolution loss, and/or other image degradations associated with conventional MD de-noising techniques. A technical effect of at least one embodiment includes recovery of at least a portion of flux loss associated with acquiring dual-energy data on scanners with limited tube capability or with decreased flux efficiency.

FIG. 1 illustrates a schematic process flow 100 for guided de-noising in accordance with various embodiments. It may be noted that the various boxes depicted in FIG. 1 may represent process steps in some embodiments and/or components or aspects configured to perform process steps in some embodiments. Generally, as seen in FIG. 1, dual-energy CT information may be received as an input in various embodiments, and an output of de-noised material images and/or a de-noised monochromatic image (or images) may be provided as an output of the process flow 100. In various embodiments, certain blocks may be omitted, and/or additional process blocks may be added (see, e.g., FIG. 5).

For the embodiment depicted in FIG. 1, at block 110, a filtered back projection is performed on dual-energy CT information acquired during a scan. In the illustrated embodiment, high-energy information $E_1$ and low-energy information $E_2$ are used to generate material decomposition images, specifically a first raw material decomposition image $m_1$ and a second raw material decomposition image $m_2$. By way of example, the first material decomposition image $m_1$ may correspond to an iodine image and the second material decomposition image $m_2$ may correspond to a water image. As part of a process including guided de-noising illustrated by the dashed lines defining block 120, the raw material decomposition images $m_1$ and $m_2$ may be de-noised to provide corresponding de-noised MD images $\hat{m}_1$ and $\hat{m}_2$.

In the illustrated embodiment, the block 120 includes a linear transformation block (block 130), a guided de-noising block (block 140), and an inverse linear transformation block (block 150). The linear transformation performed at block 130 is configured to provide a low-noise image and a high-noise image, with the low-noise image later used for guided de-noising of the high-noise image. The low-noise image may be provided via a first linear transform and the high-noise image via a second linear transform. In some embodiments, the second linear transform may be a transpose of the first linear transform. The linear transformation performed at block 130 may provide first and second monochromatic images in some embodiments; however, other transforms may be employed in other embodiments. In some embodiments, the high-noise image may be a transpose of the low-noise image. It may be noted that, as used herein, the first linear transform and second linear transform need not necessarily be separate, but may each be a portion or aspect of a common linear transform that includes both the first linear transform and the second linear transform. A transform, for example, may be applied to a set of two images to produce another set of two images, with the first linear transform being a portion of the transform used to produce the first image and the second linear transform being a portion used to produce the second image. (See, e.g., Equations (1) and (2).) Similarly, an inverse transform may be have two portions, with the first portion referred to as a first inverse transform and the second portion or aspect referred to as a second inverse transform.

In the illustrated embodiment, at block 130, a first linear transformation is performed to provide a first basis image $x_1$ and a second linear transformation is performed to provide a second basis image $x_2$ from the first raw material decomposition image $m_1$ and the second raw material decomposition image $m_2$. The first basis image $x_1$ is a low-noise image, and the second basis image $x_2$ is a high-noise image. The particular transforms employed in some embodiments are configured to provide a minimum or reduced noise level in the first basis image and a maximum, elevated, or increased noise level in the second basis image. For example, the first and second basis images may be synthetic monochromatic images generated from the first and second material images, but the noise level of the first basis image may be lower than a noise level for a monochromatic image generated for diagnostic purposes using the first and second material images, while the noise level of the second basis image may be higher than a noise level for a monochromatic image generated for diagnostic purposes using the first and second material images.

For example, the basis images may be monochromatic images generated at an optimal energy or keV level. As used herein, an optimal energy level or an optimal keV level may be understood as an energy level at which a noise level for the first linear transform is minimized relative to other energy values. The optimal energy level may correspond to the mean energy of an output spectrum after attenuation by the object being imaged. The particular relationship between optimal energy and the output spectrum may vary by system and object being imaged. Generally, in various embodiments, conventional techniques to determine the optimal energy level for a given system and object being imaged with the system may be employed. At the optimal energy, the linear transformation performed at block 130 may include an addition that generates the low-noise image $x_1$ and a subtraction used to generate the high-noise image $x_2$. For example, in the illustrated embodiment, the addition removes negatively correlated noise to provide a low noise image and the subtraction enhances negatively correlated noise to provide a high noise image. It may be noted that, in alternate embodiments, an energy level other than the optimal energy may be employed with the linear transformation.

Next, at block 140, the low noise first basis image $x_1$ is used to de-noise the high noise second basis image $x_2$ to provide a de-noised second basis image $\hat{x}_2$. For guided de-noising of the second basis image $x_2$ using the first basis image $x_1$, a filter that is at least in part defined by the first basis image $x_1$ may be applied to the second basis image $x_2$. For example, a weighting may be applied to pixels of the second basis image $x_2$, with at least one term of the weighting varying as a function of one or more corresponding pixels of the first basis image $x_1$.

Following the de-noising of the second basis image $x_2$, an inverse linear transformation (e.g., an inverse of the transformation previously performed at 130) is applied to the first basis image $x_1$ and the de-noised second basis image $\hat{x}_2$ at 150 to provide a first de-noised material image $\hat{m}1$ and a second de-noised material image $\hat{m}2$. For example, the first de-noised material image $\hat{m}1$ may be an iodine image and the second de-noised material image $\hat{m}2$ may be a water image. The de-noised material images may be an end product of the process and may be displayed to a user. Alternatively or additionally, further processing of the de-noised material images (e.g., the output of block 120) may be performed. For example, at block 160 of the illustrated embodiment, a linear transform is performed using the first de-noised material image m̂1 and the second de-noised material image m̂2 to provide a synthetic monochromatic image Î. One or more synthetic monochromatic images may be generated using the de-noised material images at one or more desired energies. It may be noted that, in some embodiments (see, e.g., FIG. 5 and related discussion), other processing or de-noising may be performed before performance of the inverse linear transformation at 150.

Various different transforms may be used in keeping with the general principles outline herein. For example, in some embodiments, a guided de-noising approach applies the principle that there exists a particular photon energy at which the corresponding linear combination of raw MD images produces a monochromatic image with minimal noise across all diagnostically interesting energy levels. That is, the negatively correlated noise in the two MD images cancels at this energy. The particular photon energy may be referred to herein as the optimal keV level, as also discussed elsewhere herein. In various embodiments, a monochromatic image at the optimal keV level may be used as the guide to perform guided de-noising.

For example, $m_1$ may be a first material decomposition image and $m_2$ may be a second material decomposition image. In various embodiments, the raw decomposition images may be water and iodine images generated using a back filtered projection of dual energy CT information acquired during a scan. Also $x_1$ and $x_2$ may be the images resulting from a linear transformation T (e.g., a linear transformation that may be performed at block 130). The linear transformation T in various embodiments may be given by:

$$\begin{bmatrix} x_1 \\ x_2 \end{bmatrix} = T \begin{bmatrix} m_1 \\ m_2 \end{bmatrix} = \begin{bmatrix} \alpha_1 & \alpha_2 \\ \beta_1 & \beta_2 \end{bmatrix} \begin{bmatrix} m_1 \\ m_2 \end{bmatrix} \quad \text{(Eq. 1)}$$

As indicated above, $x_1$ in various embodiments is the optimal keV monochromatic image, where $\alpha_1$ and $\alpha_2$ represent the coefficients for monochromatic combination at the optimal keV level. If $(\beta_1, \beta_2)=(\alpha_1, -\alpha_2)$, then the following results:

$$\begin{bmatrix} x_1 \\ x_2 \end{bmatrix} = \begin{bmatrix} \alpha_1 & \alpha_2 \\ \alpha_1 & -\alpha_2 \end{bmatrix} \begin{bmatrix} m_1 \\ m_2 \end{bmatrix} \quad \text{(Eq. 2)}$$

For this particular transformation, the correlated noise cancels in the optimal keV monochromatic image, $x_1$, while the correlated noise is magnified in the other image $x_2$. Accordingly, guided de-noising may be employed to remove the correlated noise in $x_2$ using $x_1$ as a guide.

Various de-noising filters may be employed for guided de-noising in connection with de-noising algorithms, techniques, processes and/or systems in accordance with various embodiments. Generally, several considerations may be taken into account when specifying a particular de-noising filter. First, a de-noising filter is configured to use the information from the guide image to effectively remove the correlated noise in the image to be de-noised, while still preserving true signal in the noisy image. Further, the de-noising filter should not introduce artificial structures from the guide image to the noisy image that is de-noised. Additionally, it is beneficial for the de-noising filter to be as computationally simple and efficient as possible.

In one example, a trilateral filter may be employed as a de-noising filter to accomplish the above discussed goals. The example trilateral filter calculates each pixel value in the filtered output as a linear combination of pixel values of neighboring pixels, where the combination weights are generated based on spatial distances, intensity similarities in the guide image, and intensity similarities in the image to be de-noised, between the objective pixel and neighboring pixels. Specifically, for one example trilateral filter, the filtered value of $x_2$ at pixel i is given by:

$$\hat{x}_{2,i} = \sum_j w_{ij} x_{2,j}, \quad \text{(Eq. 3)}$$

The weight, $w_{ij}$, for the example filter is given by:

$$w_{ij} = \frac{1}{z_i} \exp\left\{-\frac{(i-j)^2}{\sigma_s^2} - \frac{(x_{1,i} - x_{1,j})^2}{\sigma_r^2} - \frac{(\bar{x}_{2,i} - \bar{x}_{2,j})^2}{\sigma_q^2}\right\} \quad \text{(Eq. 4)}$$

In Equation 4, $\sigma_s$, $\sigma_r$, and $\sigma_q$ are filter parameters, and $z_i = \Sigma_j w_{ij}$ is a normalizing factor.

For the example trilateral filter, the terms within the exponential serve different functions. For example, the first term in the exponential $(-(i-j)^2/\sigma_s^2)$, is configured to account for the geometric similarity between pixel I and j, which decreases as the spatial distance of two pixels increases and therefore reduces the influence of the filter as pixels are further apart. The first term provides an example of a component of a filter that varies as a function of a distance between pixels.

The second term, $(-(x_{1,i}-x_{1,j})^2/\sigma_r^2)$, is configured to account for photometric similarities in the guide image, $x_1$. This term provides for guiding of the filtering of the image $x_2$ using the image $x_1$. For example, this term may help identify portions of the guide image that correspond to an edge or to a homogenous region. In the example filter, actual pixel values for the particular pixels are used for this term. The second term provides an example of a component of a filter that varies as a function of information from the first basis image (or guide image).

The third term, $(-(\bar{x}_{2,i}-\bar{x}_{2,j})^2/\sigma_q^2)$, is configured to account for photometric similarities in the locally averaged noise image, $\bar{x}_2$. The third term provides an example of a component of a filter that varies as a function of information from a second basis image (or image to be de-noised with a guided filter). In the example filter, locally averaged values are used for this term. It may be noted that, for example, actual values of pixels instead of locally averaged values may be used in alternate embodiments. For the second and third terms, the value decreases as the intensity difference of two pixels in corresponding images increases, which helps provide smoothing only among pixels with similar intensities.

For the example filter, the second and third terms together reflect the use of guided de-noising using information from both the guide image and the image to be de-noised. For example, $x_1$ (an optimal keV image, for example) provides a signal with good or high confidence that therefore may be used as a guide, while $x_2$ (the noisy image), though corrupted with a relatively high noise level, may still contain relatively weak but nevertheless unique information for material differentiation, and therefore should not be ignored. Thus, both the low-noise (or guide) image and the noisy image (or image to be de-noised) may be considered for generation of adequate weights for the de-noising filter, but with different confidence levels, for example $\sigma_r < \sigma_q$. Thus, with a higher confidence in the guide image (e.g., $\sigma_r < \sigma_q$), the weight $w_{ij}$ mainly depends on the optimal keV image, $x_1$, but is slightly modulated by a locally averaged version of the noisy image, $\bar{x}_2$, which is a simple estimate of the mean.

The strengths (e.g., the relative strengths) of the parameters ($\sigma_s$, $\sigma_r$, $\sigma_q$) may be tailored to achieve desired performance of the trilateral filter. For example, the parameter $\sigma_s$ controls the strength of spatial smoothing, with a larger $\sigma_s$ making the spatial kernel flatter. The parameters $\sigma_r$ and $\sigma_q$ control the influence of the guide image and the noisy image, respectively. Larger $\sigma_r$ and $\sigma_q$ introduces more smoothing, while a smaller $\sigma_r/\sigma_q$ ratio increases the influence of the guide image over the filtered noisy image. In various embodiments, the values of the parameters and/or the particular configuration of terms used may be varied, for example to provide a desired image quality, amount of de-noising, and/or computational efficiency.

It may be noted that the above discussed trilateral filter provides an example of a filter that has a first component, a second component, and a third component, wherein the first component varies as the function of the information from the first basis image, the second component varies as a function of information from the second basis image, and the third component varies as a function of a distance between pixels. In other embodiments, fewer or more components or terms may be employed. For example, in some embodiments, the first component, but not the second and third components, may be utilized, or, as another example, in some embodiments, the first and second components, but not the third component, may be employed.

Figure 2:
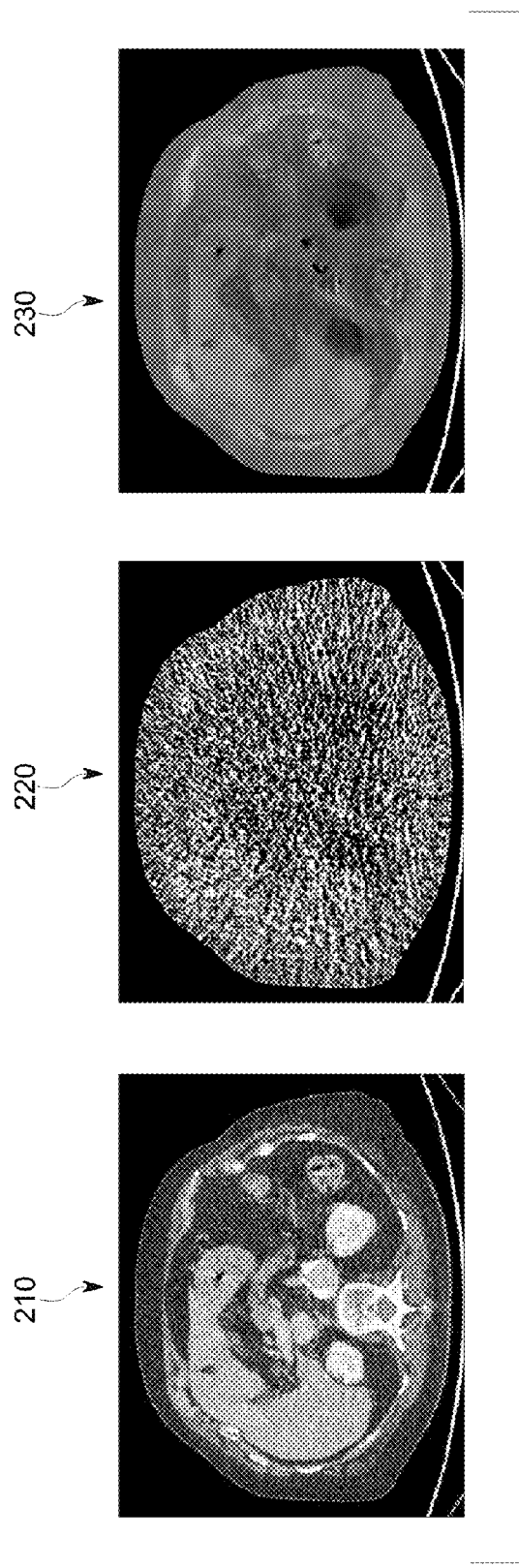
FIG. 2 illustrates results of an example guided de-noising in accordance with various embodiments.
Figure 3:
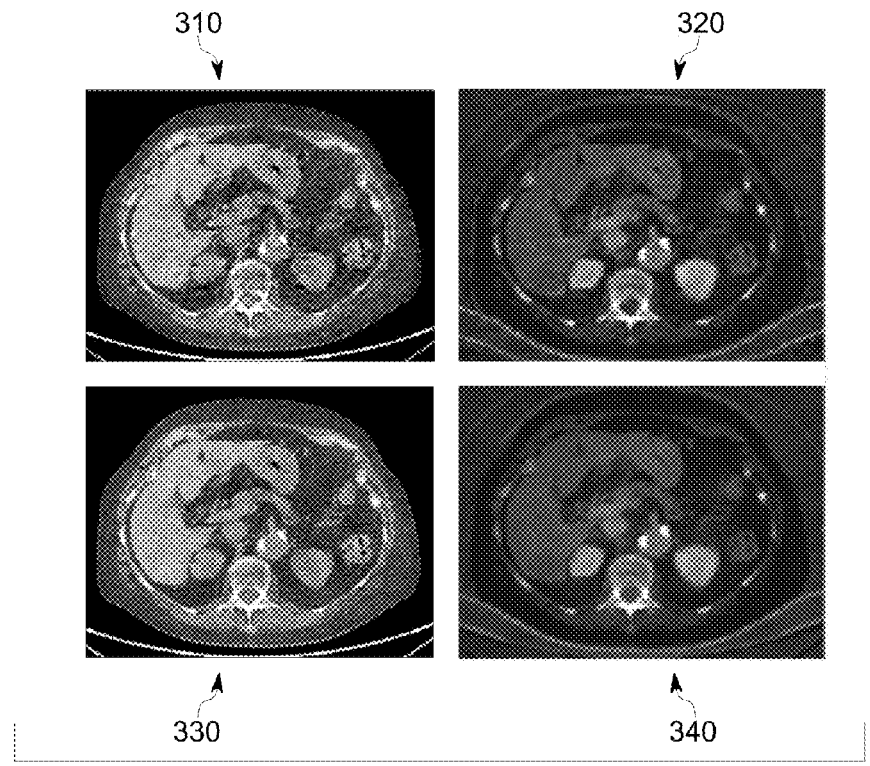
FIG. 3 provides a comparison of results between conventional de-noising and guided de-noising in accordance with various embodiments.

FIG. 2 illustrates results of an example guided de-noising in accordance with various embodiments, and FIG. 3 provides a comparison of results between conventional de-noising and guided de-noising in accordance with various embodiments. For the example depicted in FIG. 2, a guided de-noising algorithm employing a trilateral filter as described above was employed using the following parameter settings. The local averaged noise image, $\bar{x}_2$, was produced by filtering the original noisy image, $x_2$, with a 7×7 Gaussian filter with a standard deviation of 2. $\sigma_s$ was set to 9, for all cases, and $\sigma_r$ was set at 20 for a high dose case and at 80 for a low does case. Further, the parameter $\sigma_q$ was set by the following equation:

$$\sigma_q = \min\left\{\max\left\{\frac{5\sigma_r^2}{\sigma_p}, 2\sigma_r\right\}, 4\sigma_r\right\} \quad \text{(Eq. 5)}$$

In Equation 5, $\sigma_p$ is the local standard deviation in the guide image calculated by using a 7×7 sliding window. In this example, for a local region with larger variation in the guide image, the filtered noisy image contributes with higher influence than in other regions, in order to help preserve edges or structures. The lower bound of $\sigma_p$ restricts the influence of the noisy image to ensure sufficient noise reduction, while the upper bound of $\sigma_p$ ensures certain contribution from the noisy image to recover unique signal that is missing in the guide image.

For the example of FIGS. 2 and 3, a low dose clinical abdominal scan was performed. FIG. 2 shows the input and output of the trilateral filter. In FIG. 2, a guide image 210 used for de-noising an input noisy image 220 is shown. In the illustrated embodiment, the guide image 210 is a 70 keV synthetic monochromatic image, and the input noisy image 220 was generated from subtraction of material decomposition images. An output de-noised image 230 is also shown in FIG. 2. The output de-noised image 230 and input guide image 210, for example, may be utilized to generate de-noised material decomposition images, which may in turn be utilized to generate a de-noised monochromatic image. FIG. 3 shows a comparison between conventional de-noising results and results of an example embodiment. Image 310 is a water image obtained via conventional techniques, and image 320 is an iodine image obtained via conventional techniques. Also, image 330 is a water image obtained using guided de-noising in accordance with various embodiments, and image 340 is an iodine image obtained using guided de-noising in accordance with various embodiments. As seen in FIG. 3, the images 330 and 340 have lower noise and better texture without compromise of spatial resolution, in comparison with the images 310 and 320.

Figure 4:
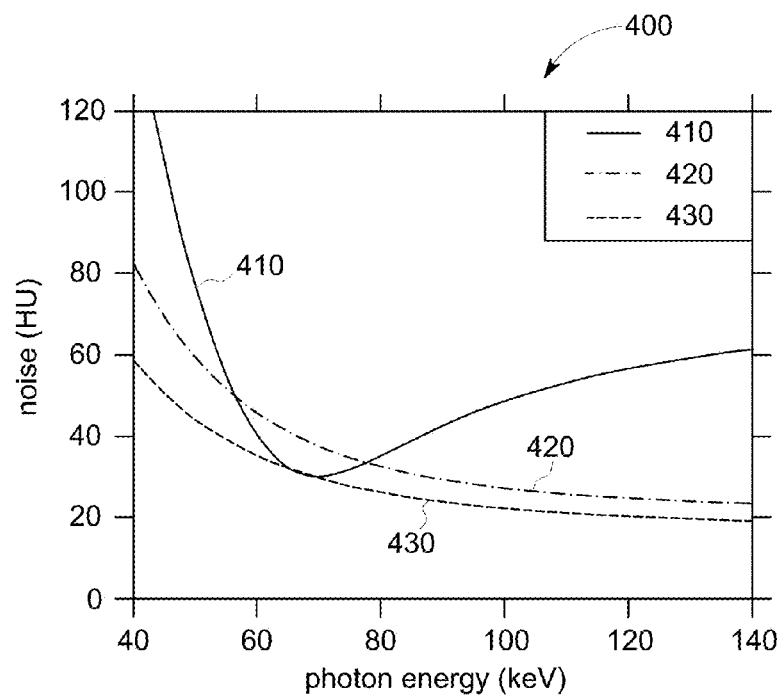
FIG. 4 illustrates a graph comparing noise measured in monochromatic images across different photon energies that have been synthesized from MD images.

FIG. 4 illustrates a graph 400 comparing noise measured in monochromatic images across different photon energies that have been synthesized from MD images. In FIG. 4, the first curve 410 depicts noise in raw (e.g., not de-noised) synthesized monochromatic images, the second curve 420 depicts noise in synthesized monochromatic images produced using conventional de-noising techniques, and the third curve 430 depicts noise in synthesized monochromatic images de-noised using guided de-noising in accordance with an example embodiment. The noise measurements of the graph 400 were taken within a homogeneous region with a liver. As seen in FIG. 4, the monochromatic images de-noised using guided de-noising contain consistently lower noise than those from the raw or conventionally de-noised images across the range of the keV spectrum.

As also mentioned above, various aspects of algorithms, processes, or systems for de-noising may be varied for different embodiments. For example, instead of the transform described by Equation 1 above, a different transform may be employed. In some embodiments, the following orthogonal transformation may be utilized:

$$T = \begin{bmatrix} \alpha_1 & \alpha_2 \\ \alpha_2 & -\alpha_1 \end{bmatrix} \quad \text{(Eq. 6)}$$

As another example, the photon energy of synthesized monochromatic images may differ from the optimal keV for all or a portion of a transform. For example, the following transform may be employed in various embodiments:

$$T = \begin{bmatrix} \alpha_1(\epsilon_{opt}) & \alpha_2(\epsilon_{opt}) \\ \alpha_1(\epsilon) & \alpha_2(\epsilon) \end{bmatrix} \quad \text{(Eq. 7)}$$

In Equation 7, $\epsilon_{opt}$ is the optimal photon energy and $\epsilon$ is a different photon energy. A further possible transformation that may be used to generate basis images is to work directly from the low-energy and high-energy kVp images instead of the material images to form the guide image. For example, the linear combination of low and high kVp images may provide a computationally cheaper alternative for producing a guide image relative to using the material images, which require a more time-consuming MD (material decomposition) process, and which may also require more data.

As one more example, the image where guided de-noising takes place may be a material image, instead of applying a transformation (e.g., the transformation of Equation 1). In such a case, the principle of negative correlation in noise between images is not relied upon, but guided de-noising may still be effective and/or provide for improved de-noising. Further still, guided de-noising may be performed in a single kVp domain.

Further still, the various parameters of a trilateral filter may be adjusted for various embodiments. For example, the parameter $\sigma_s$ controls the strength of spatial smoothing, with larger values introducing heavier smoothing. In the above discussed example, the parameter $\sigma_s$ was fixed. However, the parameter may not be fixed in other embodiments. For example, the parameter may be designed as function of the actual voxel size. In some embodiments, a smaller $\sigma_s$ may be used for images with larger voxel size, or for a larger field-of-view (FOI), to reduce or avoid loss of detail. Further, the parameter may also be designed as adaptive to actual noise level of the optimal keV image, with a larger value for higher noise level, as higher noise level may also have stronger spatial correlation and consequently benefit from heavier spatial smoothing.

Further still, the windowing due to the infinite support of Gaussian function may be considered when configuring $\sigma_s$. For example, in some embodiments, a 2D rectangular window may be utilized to cover a range of $[-3\sigma_s, +3\sigma_s]$ in both dimensions (e.g., a 55×55 rectangular window may be used for $x=\sigma_s$). Though such a large window may avoid spectral leakage, such a large window may include an unnecessarily large number of zero elements that may potentially increase computational expense. In some embodiments, the potentially increased computational expense may be addressed via use of a 2D hamming/hanning window, which provides a smaller window but still avoids or reduces spectral leakage.

As another example, the parameter $\sigma_r$ controls the smoothing strength related to intensity of the guide signal, with large values introducing more smoothing across different intensities. In some embodiments, as discussed herein, the parameter $\sigma_r$ may vary among different cases with different dose levels, and may be empirically determined. For example, as discussed above, $\sigma_r=20$ may be used for high dose cases and $\sigma_r=80$ for low dose cases. In various embodiments, however, $\sigma_r$ may be configured as explicitly related to the noise level in the optimal keV signal. Such a configuration may require an estimation of the noise level. Further, $\sigma_r$ may be configured as spatially varying adaptive to local variation in the guide signal. For example, a smaller $\sigma_r$ may be used for a local region with larger variation that may indicate an edge to avoid over-smoothing.

As yet another example, the parameter $\sigma_q$ controls the smoothing strength related to intensity of the noisy signal, which also controls the influence of the noisy signal over the guide signal. Larger values of $\sigma_q$ introduce more smoothing across different intensities, while larger $\sigma_r/\sigma_q$ ratios reduce the influence of the noisy signal over the guide signal. Potential variations in the configuration of $\sigma_q$ include use of different upper and lower bounds for $\sigma_q$ (for example, upper and lower bounds for Eq. 5), and/or varying a window size for calculating $\sigma_q$ based on actual voxel size and/or noise level.

Yet further still, in various embodiments, different techniques for calculating $\bar{x}_2$ may be employed. As discussed above, $\bar{x}_2$ is an estimate of the mean of the noisy signal, and used in conjunction with calculation of the weights of the trilateral filter. In an above discussed example, a 7×7 Gaussian filter with a standard deviation of 2 was used to obtain a local average of the noisy signal. However, in alternate embodiments, the filter size and strength, for example, may be proportional to the noise level and/or inversely proportional to the actual voxel size.

In some embodiments, a 3D de-noising filter (e.g., 3D trilateral filter) may be employed. Use of a 3D filter may provide improved noise reduction and detail preservation, for example because edges tend to have better spatial correlation than noise in 3D. However, use of a 3D filter may increase computational requirements.

Further still, the filter design may include fewer terms than specified by the example trilateral filter discussed herein, or may include additional constraints based on desired relationships between $x_1$, $x_2$, and $\bar{x}_2$. Also, the weight computation terms may include other mathematical components than the exponentials described in Equation 4. For example, other mathematical techniques may be employed to multiply the components together to form the filter weights, thus modifying the form of the disclosed trilateral filter to other general filter formulations with multi-dimensional inputs.

Figure 5:
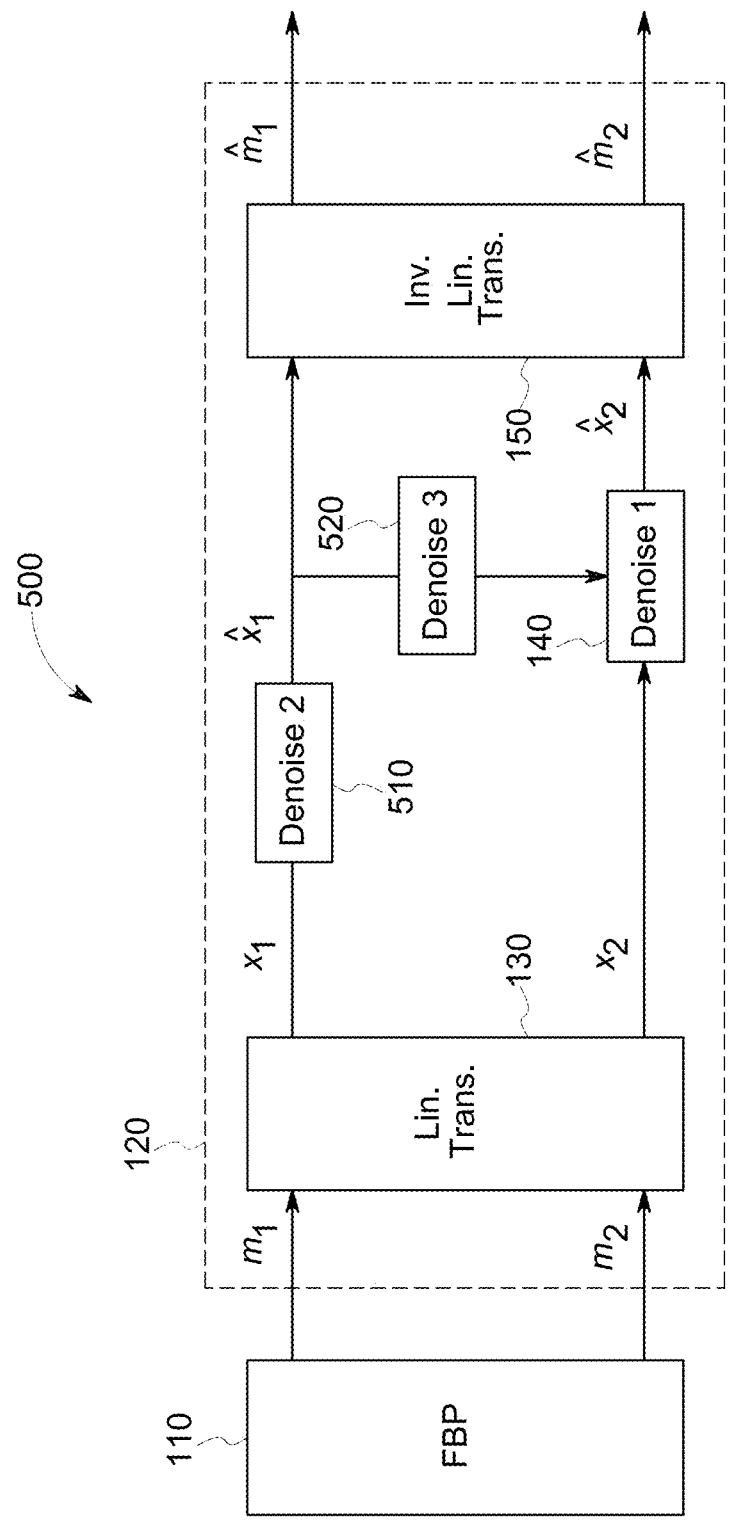
FIG. 5 illustrates a schematic process flow for guided de-noising in accordance with various embodiments.

It may also be noted that additional de-noising and/or other forms of processing of basis images used in guided de-noising may be utilized in various embodiments. FIG. 5 illustrates a schematic process flow 500 for guided de-noising in accordance with various embodiments. It may be noted that the various boxes depicted in FIG. 5 may represent process steps in some embodiments and/or components or aspects configured to perform process steps in some embodiments. The process flow 500 may be generally similar to the flow 100 discussed herein in connection with FIG. 1, with like numbered or labelled aspects being generally similar; however, the process flow 500 includes additional processing blocks use in conjunction with the first basis image $x_1$ or guide image (e.g., the image used as a guide in de-noising a different image).

In the embodiment depicted in FIG. 5, the process flow 500 includes a block 510 and a block 520 in addition to blocks already discussed herein in connection with FIG. 1. For the blocks 510 and 520, additional de-noising, other filtering, and/or other processing may be performed. At block 510, a filtering process is performed on the guide image $x_1$ to provide a modified guide image $\hat{x}_1$. The modified guide image $\hat{x}_1$ is provided to block 520 for additional de-noising before use as a guide for guided de-noising of $x_2$ to provide $\hat{x}_2$. Additionally, the modified guide image $\hat{x}_1$ is provided along with the de-noised image $\hat{x}_2$ to block 150, where an inverse linear transformation is performed using $\hat{x}_1$ and $\hat{x}_2$ to provide de-noised material images (e.g., water and iodine images). It may be noted that the additional processing (e.g., performed at block 510 and/or at block 520) may additionally or alternatively include processing other than de-noising, such as edge enhancing or Gaussian smoothing, among others.

For the illustrated embodiment, at block 510, additional filtering for the guide image or guide signal is performed. For example, the block 510 may correspond to an edge-preserving filter. The filtering at block 510 may beneficially suppress uncorrelated noise in the guide image or signal and consequently lead to MD images with reduced noise levels. As shown in FIG. 5, the result of block 510 is also utilized by block 150 in performing the inverse linear transform that provides the material images. Accordingly, the filter performed at block 510 may be configured to avoid or minimize any loss of actual signal and to avoid or minimize creation of artifacts.

Also for the illustrated embodiment, an additional filter may be provided as shown at block 520. The filter at block 520, for example, may be configured as a simple smoothing filter. The additional filter at block 520 in the illustrated embodiment receives a guide signal or image (or modified guide signal or image, for example, for embodiments including block 510 as shown in FIG. 5), and produces a smoothed signal as an output, with the output of block 520 used to guide de-noising of the noisy signal at block 140. The depicted filter 520 is utilized for guided de-noising but not in connection with the inverse linear transform for producing the material images performed at block 150. The filtering performed at block 520 may provide slight smoothing in the guide signal to help with the de-noising performance of the filtering performed at 130; however, since the filtering performed at block 520 has no direct impact on the material images generated by block 150, the filtering may be configured as a simple linear smoothing, for example, a small Gaussian kernel.

The filtering performed at block 510, as well as the filtering performed at block 520, provide examples of performing additional processing on the first basis image to provide a modified basis image for use as part of guided de-noising. Also, the filtering performed at block 510 provides an example of performing additional processing on the first basis image before performing the first and second inverse linear transforms to provide the material images. Other combinations or positions of additional processing blocks may be utilized in various embodiments.

Figure 6:
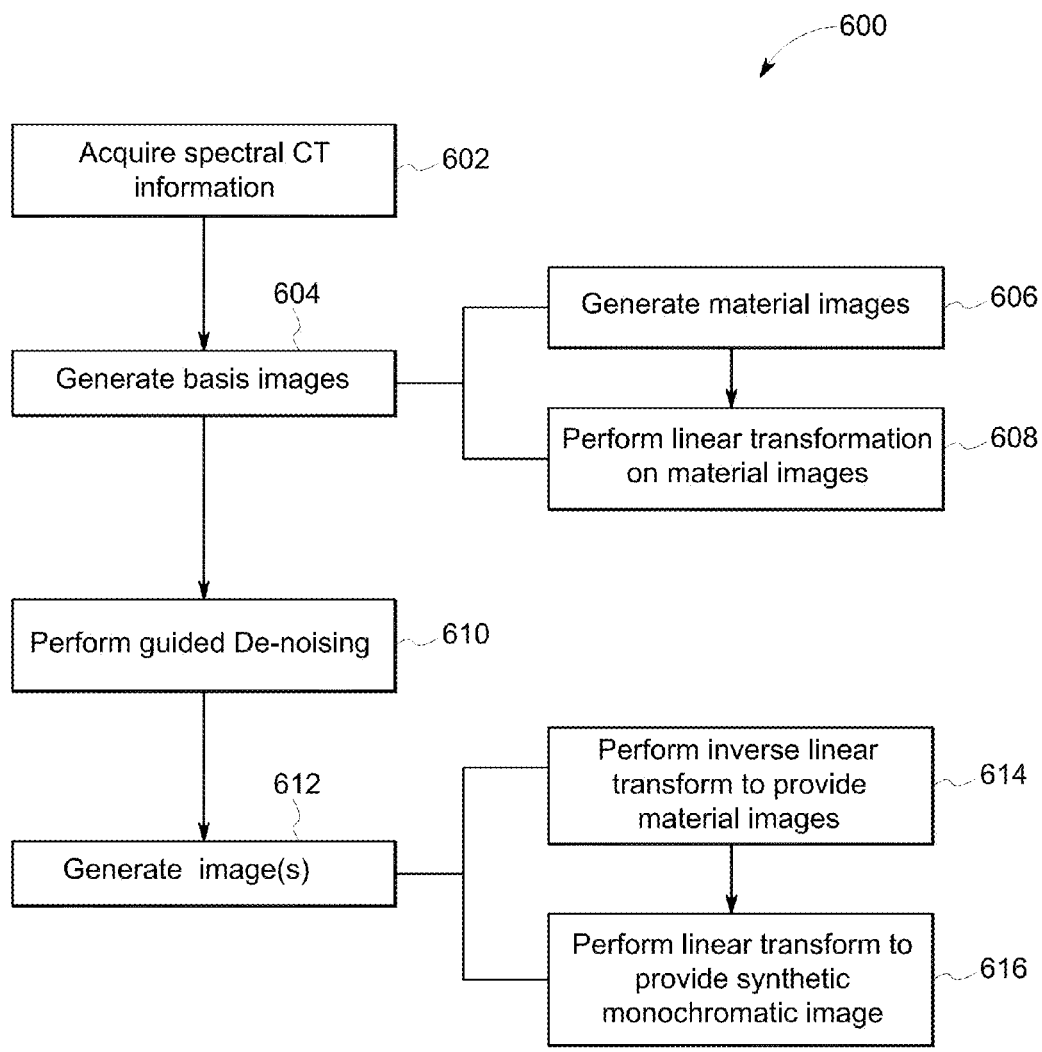
FIG. 6 is a flowchart of a method in accordance with various embodiments.

FIG. 6 provides a flowchart of a method 600 for imaging an object, in accordance with various embodiments. The method 600, for example, may employ or be performed by structures or aspects of various embodiments (e.g., systems and/or methods and/or process flows) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware (e.g., one or more aspects of the processing unit 720) to perform one or more operations described herein.

At 602, spectral CT information is acquired using a CT acquisition unit that includes an X-ray source and detector that rotate about an object to be imaged (e.g., on a gantry). In some embodiments, the X-ray source (or sources) is configured to produce X-rays at more than one energy (e.g., to produce at least two spectrums of energy having different maximum energies). In various embodiments, the X-ray source may be configured for dual-energy CT and provide X-rays at a first, higher energy level and at a second, lower energy level. For example, dual-energy CT information may be acquired in some embodiments by alternating tube energy at different rotational positions to provide interleaved information (e.g., alternating tube energy at every other rotational position of a rotating CT gantry). In other embodiments, one energy level may be employed for a complete rotation and a different energy level employed for a subsequent rotation. As another example, two or more X-ray tubes providing different energies, along with corresponding detectors, may be used. As one more example, detectors may be utilized that absorb one range of energy while passing other ranges on to other detectors to acquire spectral CT information.

At 604, basis images are generated. For example, one basis image having a relatively lower impact of one or more artifacts may be generated, and another basis image having a relatively higher impact of one or more artifacts may be generated. For instance, in the depicted embodiment, the basis images are generated to provide one basis image having a minimal or low noise level (a guide image) and another basis image having a maximum, elevated, or high noise level (a noisy image to be de-noised). The basis images are also configured such that each basis image contains at least some useful information not contained in the other basis image. It may be noted that for dual-energy scans, the high-energy projection data typically is less noisy than the low-energy projection data. Accordingly, in one example, high-energy data may be used for a first basis image or guide image, and low-energy data may be used for a second basis image to be de-noised using a guided de-noising technique as discussed herein. In some embodiments, dual-energy CT information may be further processed to provide basis signals, for example using one or both of substeps 606 and 608 depicted in FIG. 6.

At 606 of the illustrated embodiment, material images are generated, for example using a filtered back projection (see, e.g., block 110 of FIG. 1 and related discussion). The material images may be generated based on the different variations of attenuation as a function of X-ray energy exhibited by different materials. For example, a water image and an iodine image may be generated. In some embodiments, the material images can be used as basis images, while in other embodiments the material images may be further processed to generate basis images for guided de-noising. In the illustrated embodiment, at 608, a linear transformation is performed (see, e.g., block 130 of FIG. 1 and related discussion) to provide a low-noise basis image and a high-noise basis image. For example, one or both basis images generated by the linear transformation may be a synthetic monochromatic image at an optimal energy level. In some embodiments, a linear transform used to generate the high-noise basis image may be a transpose of a linear transform used to generate the low-noise basis image. In some embodiments, the low-noise basis image may be generated by an additive operation, and the high-noise image may be generated by a subtractive operation.

At 610, guided de-noising is performed (see, e.g., block 140 of FIG. 1 and related discussion). In the depicted embodiment, the high-noise basis image is de-noised using the low-noise basis image as a guide. For example, a filter including one or more components may be employed, with at least one component of the filter using information from the low-noise basis image to de-noise the high-noise basis image. The filter in some embodiments may be configured as a trilateral filter as discussed herein. It may be noted that additional processing steps may be performed on the low-noise basis image and/or the high-noise basis image to further reduce noise and/or improve image quality (see, e.g., blocks 510 and 520 of FIG. 5 and related discussion). The guided de-noising provides a de-noised or modified high-noise basis image.

At 612, one or more images are generated, for example, for display to a user. In some embodiments, the de-noised image may be displayed to a user. Additionally or alternatively, the de-noised image may be used to generate one or more additional images. The de-noised image may be used in conjunction with the low-noise basis image (or a further processed or modified version thereof) to generate one or more final images. In the illustrated embodiment, at 614, an inverse linear transform (see, e.g., block 150 of FIG. 1 and related discussion) to provide material images which may be displayed. Additionally or alternatively, the material images may be used to generate one or more synthetic monochromatic images (e.g., a monochromatic image at a predetermined energy level, such as the optimal energy level). For example, in the illustrated embodiment, at 616, a linear transform is performed using the first or low-noise basis image along with the second or de-noised basis image to provide a synthetic monochromatic image (see, e.g., block 160 of FIG. 1 and related discussion).

Figure 7:
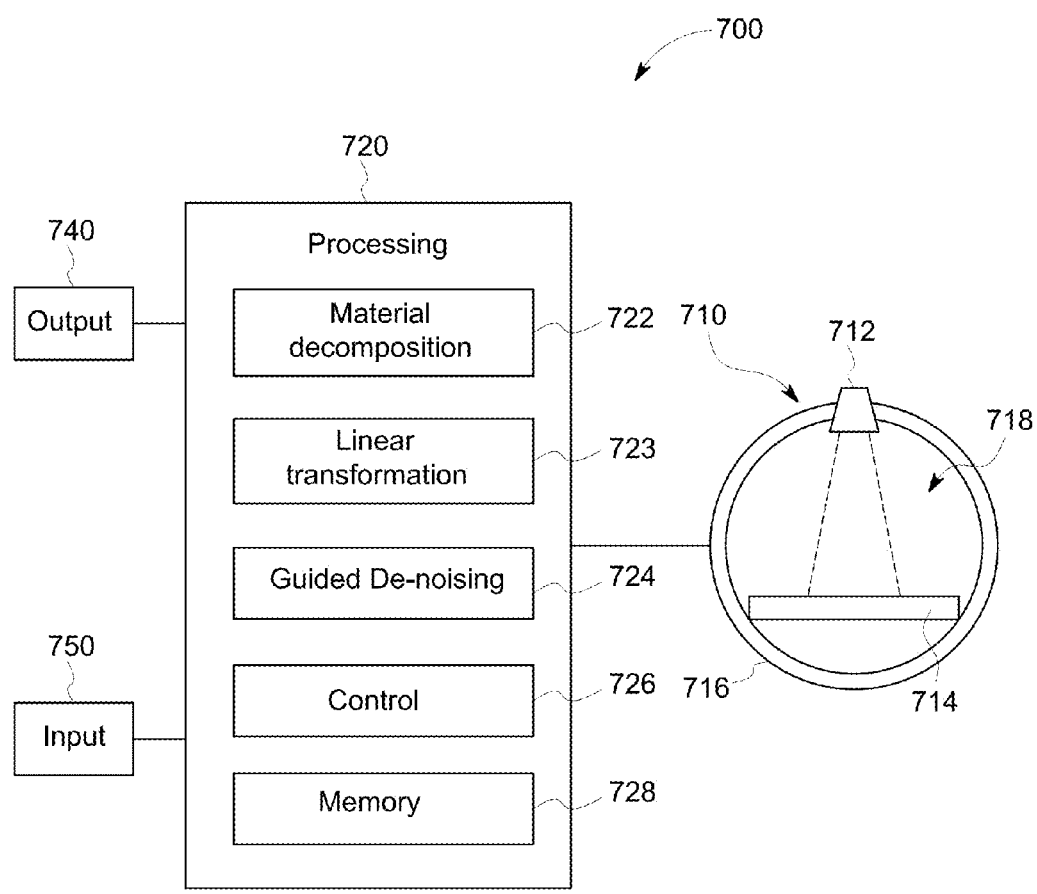
FIG. 7 is a schematic block diagram illustrating an imaging system in accordance with various embodiments.

FIG. 7 illustrates an imaging system 700 in accordance with an embodiment. The imaging system 700 may be utilized to perform or implement one or more aspects of the process flow 100, the process flow 500, and/or the method 600 discussed herein, for example. The imaging system 700 may be configured, for example, to perform computed tomography (CT) scanning of an object, such as a human or animal patient (or portion thereof. The imaging system 700 includes a CT acquisition unit 710 and a processing unit 720. Generally, the CT acquisition unit 710 is configured to acquire projection data or imaging data at two or more energy levels (e.g., spectral CT data or spectral CT imaging information), and the processing unit 720 is configured to reconstruct images using the data acquired by the CT acquisition unit 710. It may be noted that various embodiments may include additional components, or may not include all of the components shown in FIG. 7 (for example, various embodiments may provide sub-systems for use with other sub-systems to provide an imaging system). Further, it may be noted that certain aspects of the imaging system 700 shown as separate blocks in FIG. 7 may be incorporated into a single physical entity, and/or aspects shown as a single block in FIG. 7 may be shared or divided among two or more physical entities.

The depicted CT acquisition unit 710 includes an X-ray source 712 and a CT detector 714. (For additional information regarding example CT systems, see FIG. 8 and related discussion herein.) The X-ray source 712 and the CT detector 714 (along with associated components such as bowtie filters, source collimators, detector collimators, or the like (not shown in FIG. 7)) may rotate about a central axis of a bore of a gantry 716 of the system 700.

Generally, X-rays from the X-ray source 712 may be guided to an object to be imaged through a source collimator and bowtie filter. As discussed herein, the X-ray source is configured to provide X-rays at at least two different energy levels. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 712 to control distribution of X-rays passed to the object to be imaged.

X-rays that pass through the object to be imaged are attenuated by the object and received by the CT detector 714 (which may have a detector collimator associated therewith), which detects the attenuated X-rays and provides imaging information to the processing unit 720. The processing unit 720 may then reconstruct an image of the scanned portion of the object using the imaging information (or projection information) provided by the CT detector 714. The processing unit 720 may include or be operably coupled to the output unit 740, which in the illustrated embodiment is configured to display an image, for example, one or more material (e.g., iodine or water) images and/or one or more synthetic monochromatic images generated by the processing unit 720 using imaging information from the CT detector 714. The depicted input unit 750 is configured to obtain input corresponding to a scan to be performed, with the processing unit 720 using the input to determine one or more scan settings (e.g., tube voltage, tube current, scanning rotation speed, or the like). The input unit 750 may include a keyboard, mouse, touchscreen or the like to receive input from an operator, and/or may include a port or other connectivity device to receive input from a computer or other source.

In the illustrated embodiment, the X-ray source 712 is configured to rotate about the object. For example, the X-ray source 712 and the CT detector 714 may be positioned about a bore 718 of the gantry 716 and rotated about the object to be imaged. As the X-ray source 712 rotates about the object during an imaging scan, X-rays received by the CT detector 714 during one complete rotation provide a 360 degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period for that particular view. For example, each rotation may be made up of about 1000 views or projections, with each view or projection having a duration or length of about $\frac{1}{1000}$ of a complete rotation. The X-ray source 712 may be alternated between a high energy level and a lower energy level at alternating views or projections to collect dual energy CT information. In various embodiments, other arrangements may be utilized to collect spectral CT information (see, e.g., discussion herein in connection with step 602 of method 600).

As indicated herein, the processing unit 720 is configured to control various aspects of the acquisition units and/or to reconstruct an image using information obtained via the acquisition units. For example, the processing unit 720 may be configured to reconstruct a CT image using information collected by the CT acquisition unit 710. The processing unit 720 of the illustrated embodiment is configured to perform one or more aspects discussed in connection with process flow 100, process flow 500, or method 600 (e.g., generation of high and low energy projections, generation of material decomposition images, generation of basis images, processing of basis images, guided de-noising of a high-noise basis image using a low-noise basis image, performing an inverse linear transformation to provide de-noised basis images or de-noised material images, or performing a linear transformation to provide a de-noised synthetic monochromatic image, among others).

The depicted processing unit 720 is operably coupled to the input unit 750, the output unit 740, and the CT acquisition unit 710. The processing unit 720, for example, may receive imaging data or projection data from the CT detector 714 (e.g., dual-energy CT projection data). As another example, the processing unit 720 may provide control signals to one or more aspects of the CT acquisition unit 710, such as the X-ray source 712 and CT detector 714. The processing unit 720 may include processing circuitry configured to perform one or more tasks, functions, or steps discussed herein. It may be noted that "processing unit" as used herein is not intended to necessarily be limited to a single processor or computer. For example, the processing unit 720 may include multiple processors and/or computers, which may be integrated in a common housing or unit, or which may distributed among various units or housings. It may be noted that operations performed by the processing unit 720 (e.g., operations corresponding to process flows or methods discussed herein, or aspects thereof) may be sufficiently complex that the operations may not be performed by a human being within a reasonable time period. For example, the processing of imaging data, control of an imaging acquisition unit, or performance of filtering, back projection, linear transforms, or inverse linear transforms may rely on or utilize computations that may not be completed by a person within a reasonable time period.

The depicted processing unit 720 is configured to control the CT acquisition unit 710 to collect dual-energy CT information during an imaging scan.

In the illustrated embodiment, the processing unit includes a material decomposition module 722, a linear transformation module 723, a guided de-noising module 724, a control module 726, and a memory 728. It may be noted that other types, numbers, or combinations of modules may be employed in alternate embodiments, and/or various aspects of modules described herein may be utilized in connection with different modules additionally or alternatively. Generally, the various aspects of the processing unit 720 act individually or cooperatively with other aspects to perform one or more aspects of the methods, steps, or processes discussed herein.

The depicted material decomposition module 722 is configured to acquire CT projection data from the CT acquisition unit 710, and to perform a material decomposition to provide first and second material images. For example, the material decomposition module 722 may be configured to employ a filtered back projection along with predetermined information regarding the change of attenuation for materials with energy level to generate the first and second material images. In some embodiments, one of the material images may be a water image and another material image may be an iodine image.

The depicted linear transformation module 723 is configured to perform various linear transformations and inverse linear transformations, such as those discussed elsewhere herein. For example, the linear transformation module 723 of the illustrated embodiment is configured to acquire the material images from the material decomposition module 722 and to generate a high-noise basis image and a low-noise basis image using the material images. As another example, the linear transformation module 723 may acquire one or more de-noised or otherwise modified basis images from the guided de-noising module 724, and perform an inverse transform to provide de-noised material images. Further still, the linear transformation module 723 may perform a linear transformation using de-noised material images to provide one or more de-noised synthetic monochromatic image. In some embodiments, the linear transformation module 723 may use a similar transform for generating a basis image (e.g., a low-noise or guide basis image) from a material image and a de-noised monochromatic image from a de-noised material image, while in other embodiments the linear transformation module 723 may use different transforms to generate basis images and de-noised monochromatic images.

The depicted guided de-noising module 724 is configured to perform guided de-noising as described herein. In the illustrated embodiment, the guided de-noising module 724 acquires a first, low-noise or guide basis image, along with a second, high-noise basis image from the linear transformation module 723. The guided de-noising module 724 subsequently uses the first basis image as a guide for de-noising the second basis image to provide a de-noised or modified second basis image. For example, the guided de-noising module may apply, to the second basis image, a filter that includes a weighting that varies as a function of information from the first basis image. The filter may be a trilateral filter as discussed herein. The guided de-noising module 724 may perform additional processing steps on one or more basis images as discussed herein (see, e.g., FIG. 5 and related discussion).

The depicted control module 726 is configured to control the CT acquisition unit 710 and/or other aspects of the system 100 to collect spectral CT projection data or information. For example, the X-ray source 712 may be alternated between high and low energies during rotation of a gantry to acquire dual-energy CT information.

The memory 728 may include one or more computer readable storage media. The memory 728, for example, may store acquired CT information, values of parameters to be used in performing various aspects of the process flows or methods discussed herein, image data corresponding to images generated, results of intermediate processing steps, or the like. Further, the process flows and/or flowcharts discussed herein (or aspects thereof) may represent one or more sets of instructions that are stored in the memory 728 for direction operations of the system 700.

The output unit 740 is configured to provide information to the user. The output unit 740 may be configured to display, for example, one or more material images, de-noised material images, or de-noised synthetic monochromatic images, among others. The output unit 740 may include one or more of a screen, a touchscreen, a printer, or the like.

The input unit 750 may be configured to obtain an input that corresponds to one or more settings or characteristics of a scan to be performed, and to provide the input (or information corresponding to the input) to the processing unit 720, which may use the input to determine, adjust, or select the one or more parameters to be used in acquiring or processing imaging data. The input may include, for example, a portion of the body to be scanned (e.g., head, body). As another example, the input may include one or more parameter values to be used for guided de-noising, and/or information from which one or more such parameter values may be determined. The input unit 750 may be configured to accept a manual user input, such as via a touchscreen, keyboard, mouse, or the like. Additionally or alternatively, the input unit 750 may receive information from another aspect of the imaging system 700, another system, or a remote computer, for example, via a port or other connectivity device. The input unit 750 may also be configured to obtain user approval or denial of a proposed scanning setting.

Figure 8:
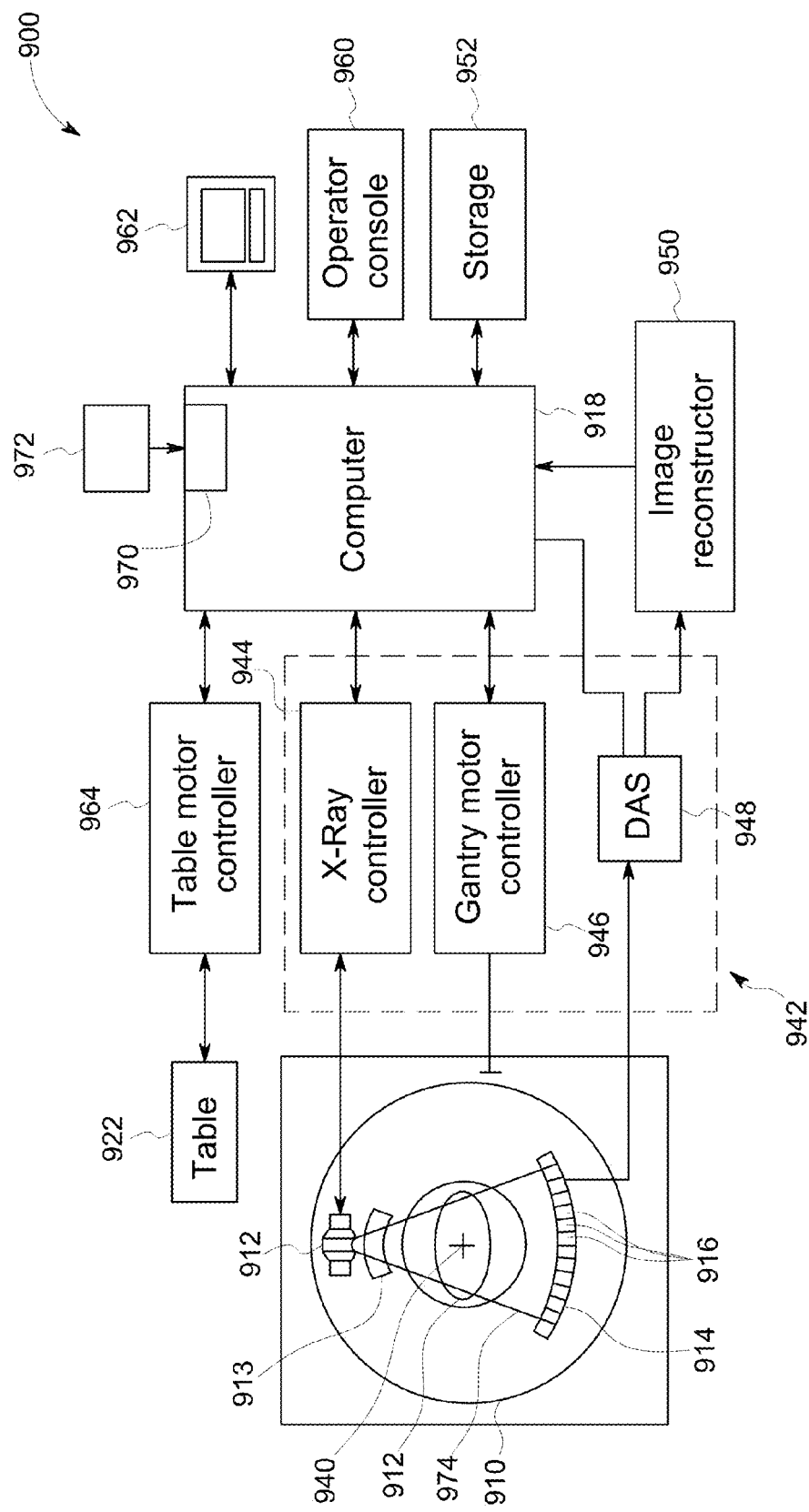
FIG. 8 is a schematic block diagram of an imaging system in accordance with various embodiments.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module 915 are provided proximate the X-ray source 912.

The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 720, or be operably coupled to one or more aspects of the processing unit 720. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 720 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
   obtaining spectral computed tomography (CT) information via an acquisition unit comprising an X-ray source and a CT detector;
   generating, with one or more processing units, using at least one image transform, a first basis image and a second basis image using the spectral CT information;
   performing, with the one or more processing units, guided processing on the second basis image using the first basis image as a guide to provide a modified second basis image;
   performing a first inverse image transform using the first basis image and the modified second basis image to provide a first modified image; and
   performing a second inverse image transform using the first basis image and the modified second basis image to provide a second modified image.

2. The method of claim 1, wherein the spectral CT information includes dual energy CT information including first energy projection data and second energy projection data corresponding to first and second energies, respectively, and wherein generating the first basis image and the second basis image using at least one image transform comprises:
   performing a first material decomposition to provide a first material image using the first energy projection data and the second energy projection data;
   performing a second material decomposition to provide a second material image using the first energy projection data and the second energy projection data; and
   performing a first image transform using the first material image and the second material image to provide the first basis image; and
   performing a second image transform using the first material image and the second material image to provide the second basis image.

3. The method of claim 2, wherein the first image transform is a linear transform configured to provide a monochromatic image at an optimal keV level, wherein the optimal keV level corresponds to an energy value at which a noise level for the first linear transform is minimized relative to other energy values.

4. The method of claim 3, wherein the second image transform is a transpose of the first linear transform.

5. The method of claim 4, wherein the first linear transform corresponds to an addition of the first material image and the second material image, and wherein the second linear transform corresponds to a subtraction of the first material image and the second material image.

6. The method of claim 1, further comprising performing additional processing on the first basis image to provide a modified first basis image, and wherein performing the guided processing comprises using the modified first basis image.

7. The method of claim 1, wherein performing the guided processing comprises filtering the second basis image with a filter having a weighting that varies as a function of information from the first basis image.

8. The method of claim 7, wherein the weighting is further configured to vary as a function of information from the second basis image.

9. The method of claim 7, wherein the weighting is configured as a tri-lateral filter having a first component, a second component, and a third component, wherein the first component varies as the function of the information from the first basis image, the second component varies as a function of information from the second basis image, and the third component varies as a function of a distance between pixels.

10. The method of claim 1, wherein the first basis image has a first noise level and the second basis image has a second noise level that is higher than the first noise level.

11. The method of claim 10, wherein performing the guided processing comprises performing a guided de-noising on the second basis image using the first basis image.

12. An imaging system comprising:
a computed tomography (CT) acquisition unit comprising an X-ray source and a CT detector configured to collect spectral CT information of an object to be imaged, the X-ray source and CT detector configured to be rotated about the object to be imaged and to collect a series of projections of the object at plural energy levels as the X-ray source and CT detector rotate about the object to be imaged; and
a processing unit comprising at least one processor operably coupled to the CT acquisition unit, the processing unit configured to:
control the CT acquisition unit to collect the spectral CT information of the object to be imaged,
generate, using at least one image transform, a first basis image and a second basis image using the spectral CT information;
perform guided processing on the second basis image using the first basis image as a guide to provide a modified second basis image; and
performing at least one inverse transform using the first basis image and the modified second basis image to generate at least one modified image.

13. The imaging system of claim 12, wherein the spectral CT information includes dual energy CT information including first energy projection data and second energy projection data corresponding to first and second energies, respectively, and wherein the processing unit is further configured to:
perform a first material decomposition to provide a first material image using the first energy projection data and the second energy projection data;
perform a second material decomposition to provide a second material image using the first energy projection data and the second energy projection data;
perform a first image transform using the first material image and the second material image to provide the first basis image; and
perform a second image transform using the first material image and the second material image to provide the second basis image.

14. The imaging system of claim 13, wherein the first image transform is a linear transform configured to provide a monochromatic image at an optimal keV level, wherein the optimal keV level corresponds to an energy value at which a noise level for the first linear transform is minimized relative to other energy values.

15. The imaging system of claim 12, wherein the processing unit is configured to perform the guided processing by filtering the second basis image with a filter having a weighting that varies as a function of information from the first basis image.

16. The imaging system of claim 15, wherein the weighting is configured as a tri-lateral filter having a first component, a second component, and a third component, wherein the first component varies as the function of the information from the first basis image, the second component varies as a function of information from the second basis image, and the third component varies as a function of a distance between pixels.

17. A tangible and non-transitory computer readable medium comprising one or more computer software modules configured to direct one or more processors to:
obtain spectral computed tomography (CT) information via an acquisition unit comprising an X-ray source and a CT detector;
generate, using at least one image transform, a first basis image and a second basis image using the spectral CT information;
perform guided processing on the second basis image using the first basis image as a guide to provide a modified second basis image; and
perform at least one inverse transform using the first basis image and the modified second basis image to generate at least one modified image.

18. The tangible and non-transitory computer readable medium of claim 17, wherein the spectral CT information includes dual energy CT information including first energy projection data and second energy projection data corresponding to first and second energies, respectively, and wherein the computer readable medium is further configured to direct the one or more processors to:
perform a first material decomposition to provide a first material image using the first energy projection data and the second energy projection data;
perform a second material decomposition to provide a second material image using the first energy projection data and the second energy projection data;
perform a first image transform using the first material image and the second material image to provide the first basis image; and
perform a second image transform using the first material image and the second material image to provide the second basis image.

19. The tangible and non-transitory computer readable medium of claim 17, wherein the computer readable medium is further configured to direct the one or more processors to filter the second basis image with a filter having a weighting that varies as a function of information from the first basis image to perform the guided processing.

20. The tangible and non-transitory computer readable medium of claim 19, wherein the weighting is configured as a tri-lateral filter having a first component, a second component, and a third component, wherein the first component varies as the function of the information from the first basis image, the second component varies as a function of information from the second basis image, and the third component varies as a function of a distance between pixels.

* * * * *